United States Patent [19]

Steinman et al.

[11] 4,255,442
[45] Mar. 10, 1981

[54] 2-[(METHYLSULFINYL)]-3-PHENYLINDOLES

[75] Inventors: Martin Steinman, Livingston; Pirouz Tabhaz, Cedar Grove, both of N.J.

[73] Assignee: Schering Corporation, Kenilworth, N.J.

[21] Appl. No.: 98,165

[22] Filed: Nov. 28, 1979

Related U.S. Application Data

[63] Continuation-in-part of Ser. No. 930,274, Aug. 2, 1978, abandoned, which is a continuation-in-part of Ser. No. 828,355, Aug. 29, 1977, abandoned.

[51] Int. Cl.³ .................... C07D 209/02; C07D 31/40
[52] U.S. Cl. .......................... 424/274; 260/326.12 R; 260/326.13 C
[58] Field of Search ................ 260/326.12 R; 424/274

[56] References Cited

U.S. PATENT DOCUMENTS

| 3,438,992 | 4/1969 | Shen | 260/326.12 R |
| 3,444,175 | 5/1969 | Shen | 260/326.12 R |
| 4,087,443 | 5/1978 | Brown et al. | 260/326.12 R |

OTHER PUBLICATIONS

Hirai et al., Chem. Abs. 80, 133414m (1972).

*Primary Examiner*—Mark L. Berch
*Attorney, Agent, or Firm*—Paul H. Ginsburg

[57] ABSTRACT

This invention relates to 2-[(methylsulfinyl)acetyl]-3-phenylindoles, to derivatives thereof, and to their use in treating rheumatoid arthritis and other disease states susceptible to treatment with immunosuppressants.

19 Claims, No Drawings

2-[(METHYLSULFINYL)]-3-PHENYLINDOLES

This application is a continuation-in-part application of our copending application Ser. No. 930,274, filed Aug. 2, 1978, abandoned which in turn is a continuation-in-part application of Application Ser. No. 828,355, filed Aug. 29, 1977, now abandoned.

This invention relates to compositions of matter classified in the art of chemistry as substituted 2-[(methylsulfinyl)-acetyl]-3-phenylindoles, various derivatives thereof, and to the processes for making and using such compositions as immunosuppressants.

The invention sought to be patented in one of its composition aspects resides in the chemical compounds 2-R-substituted-3-phenylindoles wherein R is representative of such groups as methylsulfinyl acetyl, methylsulfonyl acetyl, methylthiohydroxyacetyl, methylthioalkoxyacetyl, methylsulfinylhydroxyethyl and methylsulfonylhydroxyethyl.

The invention sought to be patented in another of its composition of matter aspects resides in the concept of pharmaceutical dosage forms containing a herein defined substituted 3-phenylindole in admixture with a pharmaceutical carrier suitable for an enteral or parenteral administration.

The invention sought to be patented in one of its process aspects resides in the concept of administering to a mammal suffering from rheumatoid arthritis a therapeutically effective quantity of a substituted 2-R-3-phenylindole wherein R is representative of such groups as methylsulfinylacetyl, methylsulfonylacetyl, methylthiohydroxyacetyl, methylthioalkoxyacetyl, methylsulfinylhydroxyethyl and methylsulfonylhydroxyethyl, in admixture with a pharmaceutically effective carrier.

More specifically, the tangible embodiments of this invention relate to those substituted 3-phenylindoles having the structural formula:

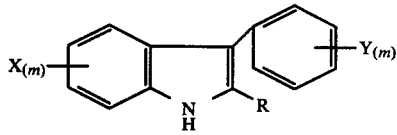

I wherein each of X and Y are halogeno, (n) is an integer of zero to three, and R is methylsulfinylacetyl, methylsulfonylacetyl, methylthiohydroxyacetyl, methylthioalkoxyacetyl, methylsulfinylhydroxyethyl, or methylsulfonylhydroxyethyl.

The term "halogeno" includes chloro, bromo, fluoro and iodo. When the benzenoid moiety is substituted with halogeno radicals it is preferred that the substituent to be located in the 5- and/or 6-positions, although mono-substitution may occur at any one of the 4-, 5-, 6-, or 7-positions and multi-substitution may also advantageously occur at the 4,5- and 4,5-and 6-positions. Preferably, mono-substitution on the 3-phenyl substituent is at the 2-position, and multi-substitution is at the 2,6-positions. Preferably, the benzenoid moiety is substituted with chloro and bromo radicals whilst fluoro is the preferred 3-phenyl substituent. The "R" radicals are derivatives of the methylsulfinylacetyl radical and are illustrated as follows:

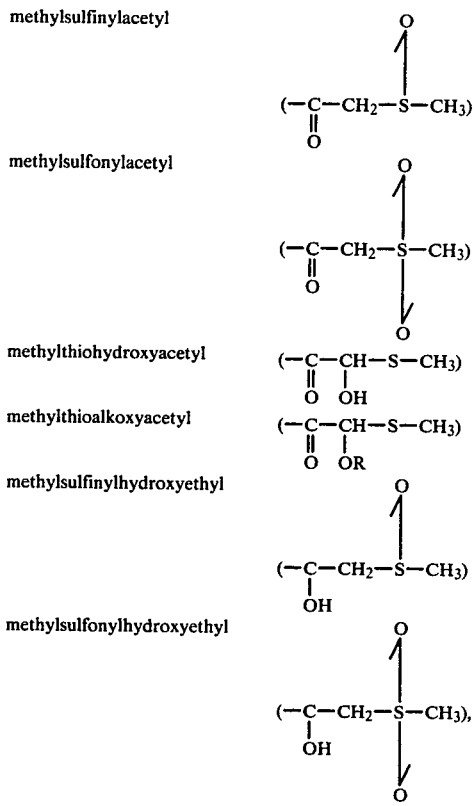

lower alkyl having up to six carbon atoms, preferably methyl.

In general, the compounds wherein R represents methylsulfinylacetyl may be prepared by reacting alkyl esters of the appropriate X, Y substituted-3-phenylindole-2-carboxylates (IV) with an anion of dimethylsulfoxide (III); the anion being a freshly prepared reactant which is obtained by warming dimethylsulfoxide in an inert organic solvent under an atmosphere of nitrogen in the presence of a base. Preferably, the warming takes place for about two hours at 65°–75° C. in a suitable solvent such as benzene. A preferred base is sodium hydride, although other equivalently functioning bases were known in the art may also be used. In effecting the reaction of the dimethylsulfoxide anion and the alkyl ester of 3-phenylindole-2-carboxylates (IV) the reactants are stirred together in an inert solvent at room temperature until reaction is complete (generally about 1–2 hours). Preferably the anion is present in excess molar quantities (about 3 times) relative to the amount of the 3-phenylindole-2-carboxylate reactant. Following completion, the reaction mixture is quenched with water, the solutions acidified and the desired product isolated by filtration and purification by crystallization. This reaction may be schematically represented as follows:

Reaction Scheme A:

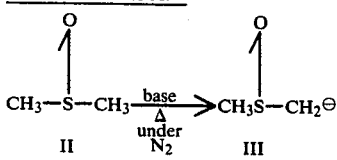

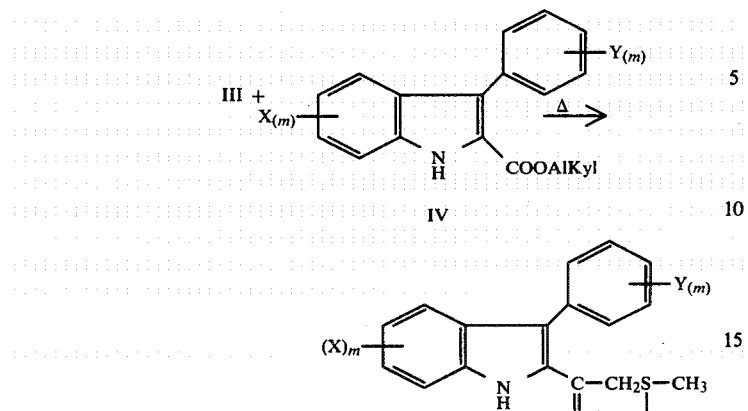

wherein X, Y, (n) are as previously defined.

The alkyl X,Y-substituted-3-phenylindole-2-carboxylates (IV) are either known compounds or may be made according to techniques analogously known in the art. In essence appropriately $X_{(n)}$ substituted phenylhydrazine acid halides are reacted with an appropriately $Y_{(n)}$-substituted alkali metal salt of a $\beta$-phenylpyruvate to produce an $X_{(n)}$, $Y_{(n)}$ substituted phenylhydrazone, which is ring cyclized to produce the desired alkyl X,Y-substituted-3-phenylindole-2-carboxylate. Often times this reaction will produce isomeric materials and in such instances the isomers are preferentially separated by chromatographic techniques. For example, the cyclization of phenylpyruvic acid 3,4-dichlorophenylhydrazone (by heating with concentrated sulfuric acid) will produce a mixture containing ethyl 5,6-dichloro-3-phenylindole-2-carboxylate and ethyl 4,5-dichloro-3-phenylindole-2-carboxylate. The mixture is chromatographed from silica gel, utilizing chloroform and the isomeric materials are easily separated. Of course, other standard techniques for the separation of isomers may also be utilized.

The remaining compounds of this invention are derivatives of the foregoing 2-(methylsulfinyl)acetyl-3-phenylindoles (V) and are prepared by techniques analogously known in the art. For example, by oxidizing the 2-methylsulfinylacetyl-3-phenylindoles (V) with meta chloroperbenzoic acid there is formed the corresponding 2-methylsulfonylacetyl-3-phenylindole (VI). Alternatively the 2-methylsulfonylacetyl-3-phenylindoles may be prepared by reacting the 3-phenylindole-2-carboxylates (IV) with an anion of dimethylsulfone. These reactions may be depicted as follows:

Reaction Scheme B:

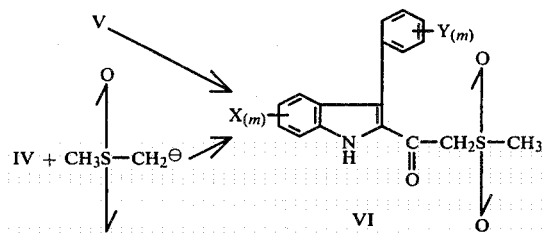

Subjecting the X,Y-substituted-2-methylsulfinyl-3-phenylindoles to the Pummerer acid rearrangement will yield, depending upon the solvent, either the corresponding 2-(methylthiohydroxyl)acetyl-3-phenylindoles (VII) or the corresponding 2-(methylthioalkoxy)acetyl-3-phenylindoles (VIII). When the Pummerer reaction is effected in water then the 2-(methylthiohydroxyl)acetyl-3-phenylindoles are obtained, but when it is effected in an alkanol, then the 2-(methylthioalkoxyl)acetyl-3-phenylindoles are prepared. These reactions may be depicted as follows:

Reaction Scheme C:

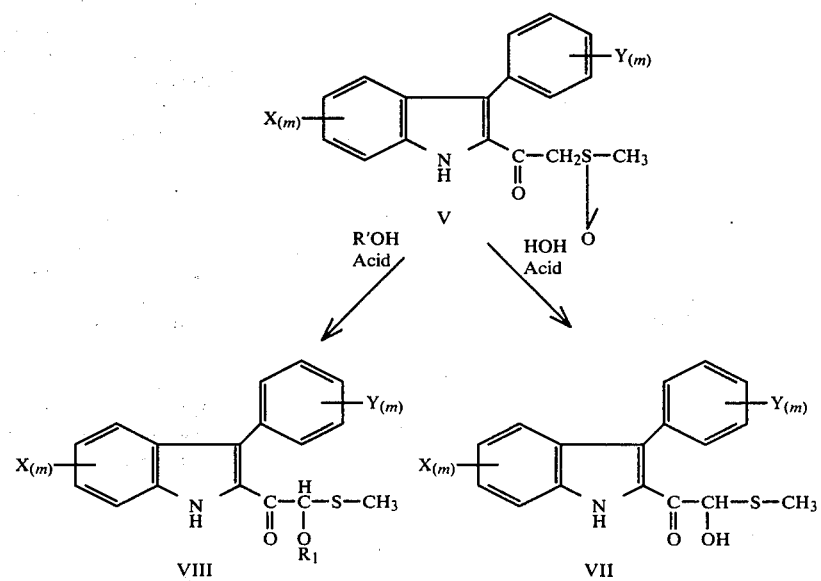

wherein X, Y, and (n) are as previously defined and $R^1$ is lower alkyl.

Alternatively, the 2-methylsulfinylacetyl (V) and the 2-methylsulfonylacetyl (VI) compounds may each be subjected to a selective chemical reduction with sodium borohydride wherein the carbonyl moiety of the 2-position substituent is preferentially reduced, i.e., neither the sulfonyl nor the sulfonyl moieties are reduced. By the selective chemical reduction the corresponding 2-methylsulfinylhydroxyethyl-3-phenylindole (IX) and the 2-methylsulfonylhydroxyethyl-3-phenylindole (X), respectively, are produced. This reaction may be schematically depicted as follows:

Reaction Scheme D:

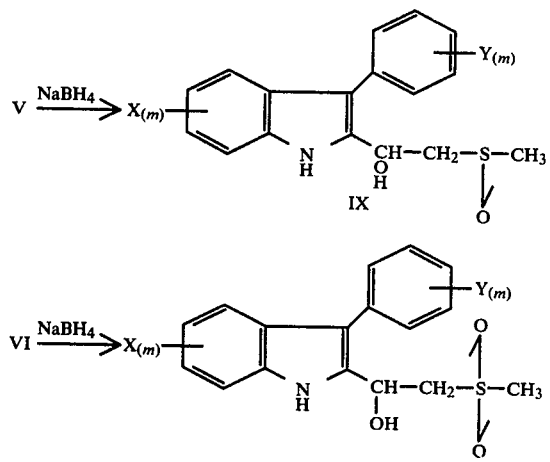

wherein X, Y and (n) are as previously defined.

Having described in generic terms the general procedures for the preparation of the compounds of the invention, the following specific examples are presented to specifically describe the details by which the compounds of this invention are prepared. Quite obviously, the examples are not meant to delineate the scope of this invention, that being done by the description throughout the entire specification.

EXAMPLE 1

PHENYLPYRUVIC ACID 3,4-DICHLOROPHENYLHYDRAZONE

Add 21.0 g of sodium β-phenylpyruvate monohydrate and 21.3 g of 3,4-dichlorophenylhydrazine hydrochloride to 300 ml of ethanol and reflux the resulting mixture for 30 minutes. Cool, add water, collect and dry the solid to yield phenylpyruvic acid 3,4-dichlorophenylhydrazone, m.p. 166°–167°.

EXAMPLE 2

ETHYL 5,6-DICHLORO-3-PHENYLINDOLE-2-CARBOXYLATE

Add 100 ml of conc. sulfuric acid to a solution of 20.0 g of phenylpyruvic acid 3,4-dichlorophenylhydrazone in 600 ml of ethanol. Reflux the mixture for 2½ hours, cool, add water, collect and dry the solid. Chromatograph on silica gel with chloroform to obtain ethyl 5,6-dichloro-3-phenylindole-2-carboxylate, m.p. 201°–202°. (Later fractions yield the isomeric ethyl 4,5-dichloro-3-phenylindole-2-carboxyate.)

EXAMPLE 3

ETHYL 6-BROMO-5-CHLORO-3-(2-FLUOROPHENYL)INDOLE-2-CARBOXYLATE

Add 1.0 ml of bromine to 4.6 g of ethyl 5-chloro-3-(2-fluorophenyl)indole-2-carboxylate in 250 ml of glacial acetic acid. Stir for 16 hours at room temperature, add water and collect the precipitate. Ws the precipitate with warm methanol. Collect the dry ethyl 6-bromo-5-chloro-3-(2-fluorophenyl)indole-2-carboxylate, m.p. 193°–194°.

Similarly, by following the teachings of Examples 1–3, with the use of the appropriate starting materials, the following compounds may also be produced:
ethyl 5-chloro-3-phenylindole-2-carboxylate,
ethyl 6-bromo-5-chloro-3-phenylindole-2-carboxylate,
ethyl 5-chloro-3-(2-fluorophenyl)indole-2-carboxylate,
ethyl 4,5,6-trichloro-3-phenylindole-2-carboxylate,
ethyl 5,6-dichloro-3-phenylindole-2-carboxylate,
ethyl 4,5-dichloro-3-phenylindole-2-carboxylate,
ethyl 5-chloro-3-(4-fluorophenyl)indole-2-carboxylate,
ethyl 6-bromo-6-chloro-3-(4-fluorophenyl)indole-2-carboxylate,
ethyl 5,6-dichloro-3-(3,4-dichlorophenyl)indole-2-carboxylate,
ethyl 5-chloro-3-(4-chlorophenyl)indole-2-carboxylate,
ethyl 6-chloro-3-phenylindole-2-carboxylate,
ethyl 5-bromo-6-chloro-3-(3-bromo-phenyl)indole-2-carboxylate,
ethyl 4,6-dibromo-3-phenylindole-2-carboxylate,
ethyl 5-chloro-3-(2,4-dichlorophenyl)indole-2-carboxylate,
ethyl 5-chloro-3-(2,6-difluorophenyl)indole-2-carboxylate,
ethyl 5-bromo-6-fluoro-3-phenylindole-2-carboxylate,
ethyl 5,6-difluoro-3-phenylindole-2-carboxylate,
ethyl 5,6-difluoro-3-(4-fluorophenyl)indole-2-carboxylate, and
ethyl 5,6-difluoro-3-(3,4-difluorophenyl)indole-2-carboxylate.

EXAMPLE 4

6-BROMO-5-CHLORO-2[(METHYLSULFINYL)ACETYL]-3-PHENYLINDOLE

Stir sodium hydride (13 g) in a mixture of dimethylsulfoxide (100 ml) and benzene (100 ml), and heat at 65°–75° for 2 hours under nitrogen. To this mixture add ethyl 6-bromo-5-chloro-3-phenylindole-2-carboxylate in dimethylsulfoxide (50 ml) and benzene (30 ml) at 15°–20° and stir the mixture at room temperature for one hour. Cool the resulting mixture to 15° C. add 50 ml of water (very slowly) and then add an additional 550 ml of water. Add 25 ml of acetic acid, stir and then filter. Wash the resulting solid with water and then hexane. Crystallize the desired product from methanol-methylene chloride to obtain 6-bromo-5-chloro-2[(methylsulfinyl)acetyl]-3-phenylindole, m.p. 169°–170°.

By substituting the ethyl 5-chloro-6-bromo-3-phenylindole-2-carboxylate with the products obtained by the techniques of Examples 1–3 and by substantially following the techniques of this example, there is produced the following compounds:
5-chloro-2[(methylsulfinyl)acetyl]-3-phenylindole,
5-chloro-2[(methylsulfinyl)acetyl]-3-(2-fluorophenyl)indole, 4,5,6-trichloro-2[(methylsulfinyl)acetyl]-3-phenylindole,
5,6-dichloro-2[(methylsulfinyl)acetyl]-3-phenylindole,
4,5-dichloro-2[(methylsulfinyl)acetyl]-3-phenylindole,
5-chloro-2[(methylsulfinyl)acetyl]-3-(4-fluorophenyl)indole,
6-bromo-5-chloro-2[(methylsulfinyl)acetyl]-3-(4-fluorophenyl)-indole,
5,6-dichloro-2[(methylsulfinyl)acetyl]-3-(3,4-dichlorophenyl)-indole,
5-chloro-2[(methylsulfinyl)acetyl]-3-(4-chlorophenyl)indole,
6-chloro-2[(methylsulfinyl)acetyl]-3-phenylindole,
5-bromo-6-chloro-2[(methylsulfinyl)acetyl]-3-(3-bromophenyl)indole,
4,6-dibromo-2-[(methylsulfinyl)acetyl]-3-phenylindole,
5-chloro-2[(methylsulfinyl)acetyl]-3-(2,4-dichlorophenyl)indole,
5-chloro-2[(methylsulfinyl)acetyl]-3-(2,6-difluorophenyl)indole,
5-bromo-6-fluoro-2[(methylsulfinyl)acetyl]-3-phenylindole,
5,6-difluoro-2[(methylsulfinyl)acetyl]-3-phenylindole,
5,6-difluoro-2[(methylsulfinyl)acetyl]-3-(4-fluorophenyl)indole, and
5,6-difluoro-2[(methylsulfinyl)acetyl]-3-(3,4-difluorophenyl)-indole.

EXAMPLE 5

6-BROMO-5-CHLORO-2[(METHYLSULFONYL)ACETYL]-3-PHENYLINDOLE

Stir a mixture of 6.0 g of 6-bromo-5-chloro-2-[(methyl-sulfinyl)acetyl]-3-phenylindole and 6.0 g of m-chloroperbenzoic acid in 150 ml of chloroform at room temperature for 2 hours. Concentrate the mixture to about 50 ml, in vacuo, and filter and wash the product with 20 ml of cold chloroform to obtain 6-bromo-5-chloro-2[(methylsulfonyl)acetyl]-3-phenylindole, m.p. 224°–225°.

By substituting the 6-bromo-5-chloro-2[(methylsulfinyl)-acetyl]-3-phenylindole with the products obtained by the techniques of Example 4 and by substantially following the techniques of this example, there are produced the following compounds:
5-chloro-2[(methylsulfonyl)acetyl]-3-phenylindole,
5-chloro-2[(methylsulfonyl)acetyl]-3-(2-fluorophenyl)indole,
4,5,6-trichloro-2[(methylsulfonyl)acetyl]-3-phenylindole,
5,6-dichloro-2[(methylsulfonyl)acetyl]-3-phenylindole,
4,5-dichloro-2[(methylsulfonyl)acetyl]-3-phenylindole,
5-chloro-2[(methylsulfonyl)acetyl]-3-(4-fluorophenyl)indole,
6-bromo-5-chloro-2[(methylsulfonyl)acetyl]-3-(4-fluorophenyl)-indole,
5,6-dichloro-2[(methylsulfonyl)acetyl]-3-(3,4-dichlorophenyl)-indole,
5-chloro-2[(methylsulfonyl)acetyl]-3-(4-chlorophenyl)indole,
6-chloro-2[(methylsulfonyl)acetyl]-3-(4-chlorophenyl)indole,
5-bromo-6-chloro-2[(methylsulfonyl)acetyl]-3-(3-bromophenyl)-indole,
4,6-dibromo-2[(methylsulfonyl)acetyl]-3-phenylindole,
5-chloro-2[(methylsulfonyl)acetyl]-3-(2,4-dichlorophenyl)indole,
5-chloro-2[(methylsulfonyl)acetyl]-3-(2,6-difluorophenyl)indole,
5-bromo-6-fluoro-2[(methylsulfonyl)acetyl]-3-phenylindole,
5,6-difluoro-2[(methylsulfonyl)acetyl]-3-phenylindole,
5,6-difluoro-2[(methylsulfonyl)acetyl]-3-(4-fluorophenyl)indole, and
5,6-difluoro-2[(methylsulfonyl)acetyl]-3-(3,4-difluorophenyl)-indole.

EXAMPLE 6

6-BROMO-5-CHLORO-2[(1-HYDROXY-2-METHYLSULFINYL)ETHYL]-3-PHENYLINDOLE

To 6-Bromo-5-chloro-2[(methylsulfinyl)acetyl]-3-phenylindole (2.5 g) in 50 l of ethanol add 0.3 g of sodium borohydride and after a solution is obtained (about 10 minutes), stir the mixture for another 30 minutes. Slowly add 1 ml of acetic acid, and then add 100 ml of water. Decant the liquid from the insoluble material, dissolve it in ethanol and add ether-hexane to obtain 6-bromo-5-chloro-2[(1-hydroxy-2-methylsulfinyl)ethyl]-3-phenylindole, m.p. 145°–148°.

By substituting the 6-bromo-5-chloro-2[(methylsulfinyl)-acetyl]-3-phenylindole reactant of this example with those products derived fro Example 4, and by substantially following the techniques of this example there is produced the following compounds:
5-chloro-2[(1-hydroxy-2-methylsulfinyl)acetyl]-3-phenylindole,
5-chloro-2[(1-hydroxy-2-methylsulfinyl)acetyl]-3-(2-fluorophenyl)-indole,
4,5,6-trichloro-2[(1-hydroxy-2-methylsulfinyl)acetyl]-3-phenylindole,
5,6-dichloro-2[(1-hydroxy-2-methylsulfinyl)acetyl]-3-phenylindole,
4,5-dichloro-2[(1-hydroxy-2-methylsulfinyl)acetyl]-3-phenylindole,
5-chloro-2[(1-hydroxy-2-methylsulfinyl)acetyl]-3-(4-fluorophenyl)-indole,
6-bromo-5-chloro-2[(1-hydroxy-2-methylsulfinyl)acetyl]-3-(4-fluorophenyl)indole,
5,6-dichloro-2[(1-hydroxy-2-methylsulfinyl)acetyl]-3-(3,4-dichlorophenyl)indole,
5-chloro-2[(1-hydroxy-2-methylsulfinyl)acetyl]-3-(4-chlorophenyl)-indole,
6-chloro-2[(1-hydroxy-2-methylsulfinyl)acetyl]-3-phenylindole,
5-bromo-6-chloro-2[(1-hydroxy-2-methylsulfinyl)acetyl[3-(3-bromophenyl)indole,
4,6-dibromo-2[(1-hydroxy-2-methylsulfinyl)acetyl]-3-phenylindole,
5-chloro-2[(1-hydroxy-2-methylsulfinyl)acetyl]-3-(2,4-dichlorophenyl)indole,
5-chloro-2[(1-hydroxy-2-methylsulfinyl)acetyl]-3-(2,6-difluorophenyl)indole,
5-bromo-6-fluoro-2[(1-hydroxy-2-methylsulfinyl)acetyl]-3-phenylindole,
5,6-difluoro-2[(1-hydroxy-2-methylsulfinyl)acetyl]-3-phenylindole,
5,6-difluoro-2[(1-hydroxy-2-methylsulfinyl)acetyl]-3-(4-fluorophenyl)indole, and
5,6-difluoro-2[(1-hydroxy-2-methylsulfinyl)acetyl]-3-(3,4-difluorophenyl)indole.

EXAMPLE 7

6-BROMO-5-CHLORO-2-[(1-HYDROXY-2-METHYLSULFONYL)-ETHYL]-3-PHENYLINDOLE

To 6-Bromo-5-chloro-2[(methylsulfonyl)acetyl]-3-phenylindole (2.2 g) in 75 ml of ethanol add 0.175 g of sodium borohydride. After a solution is obtained (about 10 minutes) stir the mixture for another 30 minutes, then slowly add 1 ml of acetic acid. Treat with charcoal, filter and add 100 ml of water to the filtrate to obtain 6-bromo-5-chloro-2[(1-hydroxy-2-methylsulfonyl)ethyl]-3-phenylindole, m.p. 187°–188°.

Similarly, by substituting the 6-bromo-5-chloro-2-[(2-methylsulfonyl)acetyl]-3-phenylindole reactant of this example with the compounds derived from the process of example 5, and by substantially following the techniques of this example, there is produced the following compounds:

5-chloro-2[(1-hydroxy-2-methylsulfonyl)ethyl]-3-phenylindole, 5-chloro-2[(1-hydroxy-2-methylsulfonyl)ethyl]-3-(2-fluorophenyl)-indole, 4,5,6-trichloro-2[(1-hydroxy-2-methylsulfonyl)ethyl]-3-phenylindole, 5,6-dichloro-2[(1-hydroxy-2-methylsulfonyl)ethyl]-3-phenylindole, 4,5-dichloro-2[(1-hydroxy-2-methylsulfonyl)ethyl]-3-phenylindole, 5-chloro-2[(1-hydroxy-2-methylsulfonyl)ethyl]-3-(4-fluorophenyl)-indole, 6-bromo-5-chloro-2[(1-hydroxy-2-methylsulfonyl)ethyl]-3-(4-fluorophenyl)indole, 5,6-dichloro-2[(methylsulfonyl)ethyl]-3-(3,4-dichlorophenyl)indole, 5-chloro-2[(1-hydroxy-2-methylsulfonyl)ethyl]-3-(4-chlorophenyl)-indole, 6-chloro-2[(1-hydroxy-2-methylsulfonyl)ethyl]-3-(4-chlorophenyl)-indole, 5-bromo-6-chloro-2[(1-hydroxy-2-methylsulfonyl)ethyl]-3-(3-bromophenyl)indole, 4,6-dibromo-2[(1-hydroxy-2-methylsulfonyl)ethyl]-3-phenylindole, 5-chloro-2[(1-hydroxy-2-methylsulfonyl)ethyl]-3-(2,4-dichlorophenyl)indole, 5-chloro-2[(1-hydroxy-2-methylsulfonyl)ethyl]-3-(2,6-difluorophenyl)indole, 5-bromo-6-fluoro-2[(1-hydroxy-2-methylsulfonyl)ethyl]-3-phenylindole, 5,6-difluoro-2[(1-hydroxy-2-methylsulfonyl)ethyl]-3-phenylindole, 5,6-difluoro-2[(1-hydroxy-2-methylsulfonyl)ethyl]-3-(4-fluorophenyl)indole, and 5,6-difluoro-2[(1-hydroxy-2-methylsulfonyl)ethyl]-3-(3,4-difluorophenyl)indole.

EXAMPLE 8

6-BROMO-5-CHLORO-3-PHENYLINDOLE-2-GLYOXAL METHYL HEMIMERCAPTAL

Slowly add 15 ml of 6 N hydrochloric acid to 6-bromo-5-chloro-2[(methylsulfonyl)acetyl]-3-phenylindole (2 g) in dimethyl sulfoxide (75 ml), stir the resulting mixture for 3 hours, quench with ice water, collect and dry the solid to yield 6-bromo-5-chloro-3-phenylindole-2-glyoxal methyl hemimercaptal, m.p. 153°–154°.

By substituting the 6-bromo-5-chloro-2[(methylsulfinyl)acetyl]-3-phenylindole with the products obtained by the techniques of Example 4, and by substantially following the techniques of this example, there is produced the following compounds:

5-chloro-3-phenylindole-2-glyoxal methyl hemimercaptal, 5-chloro-3-phenylindole-2-glyoxal methyl hemimercaptal, 5-chloro-3-(2-fluorophenyl)indole-2-glyoxal methyl hemimercaptal, 4,5,6-trichloro-3-phenylindole-2-glyoxal methyl hemimercaptal, 5,6-dichloro-3-phenylindole-2-glyoxal methyl hemimercaptal, 4,5-dichloro-3-phenylindole-2-glyoxal methyl hemimercaptal, 5-chloro-3-(4-fluorophenyl)indole-2-glyoxal methyl hemimercaptal, 6-bromo-5-chloro-3-(3-fluorophenyl)indole-2-glyoxal methyl hemimercaptal, 5,6-dichloro-3-(3,4-dichlorophenyl)indole-2-glyoxal methyl hemimercaptal, 5-chloro-3-(4-chlorophenyl)indole-2-glyoxal methyl hemimercaptal, 6-chloro-3-phenylindole-2-glyoxal methyl hemimercaptal, 5-bromo-6-chloro-3-(3-bromophenyl)indole-2-glyoxal methyl hemimertaptal, 4,6-dibromo-3-phenylindole-2-glyoxal methyl hemimercaptal, 5-chloro-3-(2,4-dichlorophenyl)indole-2-glyoxal methyl hemimercaptal, 5-chloro-3-(2,6-difluorophenyl)indole-2-glyoxal methyl hemimercaptal, 5-bromo-6-fluoro-3-phenylindole-2-glyoxal methyl hemimercaptal, 5,6-difluoro-3-phenylindole-2-glyoxal methy hemimercaptal, 5,6-difluoro-3-(4-fluorophenyl)indole-2-glyoxal methyl hemimercaptal, and 5,6-difluoro-3-(3,4-difluorophenyl)indole-2-glyoxal methyl hemimercaptal.

EXAMPLE 9

6-BROMO-5-CHLORO-2[(METHYLTHIO)(METHOXY)ACETYL]-3-PHENYLINDOLE

Add 2 ml of concentrated hydrochloric acid to 6-bromo-5-chloro-2[(methylsulfinyl)aetyl]-3-phenylindole (5.0 g) in 50 ml of methanol and 50 ml of tetrahydrofuran, warm the mixture to 60° for 2 hours. Cool, add water and the resulting solid is collected and dried to obtain 6-bromo-5-chloro-2[(methylthio)(methoxy)acetyl]-3-phenylindole, m.p. 145°–147°.

By substituting the 6-bromo-5-chloro-2[(methylsulfinyl)acetyl-3-phenylindole with the products obtained by the techniques of Exmple 5, and by substantially following the techniques of this reaction there is produced the following compounds:

5-chloro-2[(methylthio)(methoxy)acetyl]-3-phenylindole, 5-chloro-2[(methylthio)(methoxy)acetyl]-3-(2-fluorophenyl)indole, 4,5,6-trichloro-2[(methylthio)(methoxy)acetyl]-3-phenylindole, 5,6-dichloro-2[(methylthio)(methoxy)acetyl]-3-phenylindole, 4,5-dichloro-2[(methylthio)(methoxy)acetyl]-3-phenylindole, 5-chloro-2[(methylthio)(methoxy)acetyl]-3-(4-fluorophenyl)indole,
6-bromo-5-chloro-2[(methylthio)(methoxy)acetyl]-3-(4-fluorophenyl)indole,
5,6-dichloro-2[(methylthio)(methoxy)acetyl]-3-(3,4-dichlorophenyl)indole,
5-chloro-2[(methylthio)(methoxy)acetyl]-3-(4-chlorophenyl)indole,
6-chloro-2[(methylthio)(methoxy)acetyl]-3-phenylindole,
5-bromo-6-chloro-2[(methylthio)(methoxy)acetyl]-3-(3-bromophenyl)indole,
4,6-dibromo-2[(methylthio)(methoxy)acetyl]-3-phenylindole,
5-chloro-2[(methylthio)(methoxy)acetyl]-3-(2,4-dichlorophenyl)indole,
5-chloro-2[(methylthio)(methoxy)aetyl]-3-(2,6-difluorophenyl)indole,
5-bromo-6-fluoro-2[(methylthio)(methoxy)acetyl]-3-phenylindole,
5,6-difluoro-2[(methylthio)(methoxy)acetyl]-3-phenylindole,
5,6-difluoro-2[(methylthio)(methoxy)acetyl]-3-(4-fluorophenyl)indole, and
5,6-difluoro-2[(methylthio)(methoxy)acetyl]-3-(3,4-difluorophenyl)indole.

Similarly, by substituting the methanol of this example with equivalent quantities of straight and branched-chain alcohols having up to six carbon atoms, corresponding 2[(methylthio)(alkoxy)acetyl]-3-phenylindoles are produced.

The compounds of this invention have the applied use characteristic of inhibiting both antibody and cell-mediated immune reactions. The antibody immune reactions include the immune response to sheep erythrocytes and the immune responses to trinitrophenylated liposaccharide in mice as assessed by the spleen assay of Jerne, et al., Cell-bound Antibodies, Wistar Institute Press, 1963. Immune reactions classified as cell-mediated, delayed type hypersensitivities include the late secondary migratory lesions in rats injected with Freund's adjuvant (in accordance with the techniques described in British J. Pharmacology, 21:127–136 and 24:632–640), skin transplant rejection in mice and rats and mammary gland rejection (as described in Transplantation of Cells and Tissues, Wistar Institute Press, 1961), contact and protein hypersensitivities in guinea pigs, rabbits and rats (Uhr, Physiology Review, 46:359–419) and experimental allergic encephalomycelitus in rats. From these tests, as well as by comparison with known immunosuppressants the compounds are effective in suppressing the immune response at daily doses of about 1 to 100 mpk. Disease states for which the immunosuppressant activity of the compounds of this invention are useful include rheumatoid arthritis, ulcerative colitis, allergies, systemic lupus erythematosus, hemalytic anemia, Chrohn's disease, and the like. In their use as immunosuppressants the compounds have low toxicity and are non-cytotoxic at therapeutic doses. In their use, the compounds of this invention may be combined with inert pharmaceutical excipients such as lactose, mannitol, starch and other such inert pharmaceutical carriers when formulated into such dosage forms as tablets, capsules, suppositories and the like. For parenteral usage, the compounds may be formulated with an inert, pharmaceutically acceptable vehicle, such as water, saline, sesame oil and the like. These formulations may be compounded according to the techniques well known to those of ordinary skill in the pharmaceutical art. Preferably the compounds may be administered in 3–4 divided daily doses although the specific regimen will be dictated by the severity and nature of the particular disease state.

As is true in most large classes of chemical compounds useful in the treatment of diseases, certain subgeneric groups and certain specific compounds are most preferred than others. Insofar as the instant X,Y-substituted-2-R-3 phenylindoles are concerned, those compounds wherein R represents methylsulfinylacetyl or methylsulfonylacetyl are most preferred. Further, it is found that compounds having a halogeno substituent at the 5- and/or 6-positions are preferred whilst substitution of the 3-phenyl substituent is most rewarding when the Y substituent is located at the ortho position. Preferred specific compounds are 6-bromo-6-chloro-2-[(methylsulfonyl)acetyl]-3-phenylindole, 5,6-dichloro-2-[(methylsulfinyl)acetyl]-3-(3,4-dichlorophenyl)indole, 6-bromo-5-chloro-2-[(methylsulfonyl)acetyl]-3-phenylindole, 5-chloro-2-[(methylsulfinyl)acetyl]-3-(2-fluorophenyl)indole, 6-bromo-5-chloro-3-(2-fluorophenyl)-2-[(methylsulfinyl)acetyl]indole, 5,6-dichloro-2-[(methylsulfinyl)acetyl]-3-phenylindole, 4,5,6-trichloro-2-[(methylsulfinyl)acetyl]-3-phenylindole, 5-chloro-2-[(methylsulfinyl)acetyl]-3-(2,6-difluorophenyl)indole, 5-chloro-2-[(methylsulfinyl)acetyl]-3-(2,4-dichlorophenyl)indole. The least desired compounds are those wherein (n) is zero for both X and Y designations.

We claim:

1. A compound of the formula

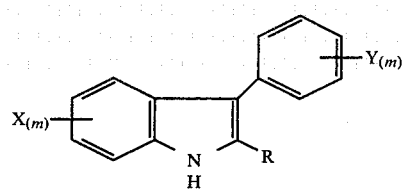

wherein each of X and Y are halogeno, (n) is an integer of zero to three, an R is methylsulfinylacetyl, methylsulfonylacetyl, methylthiohydroxyacetyl, methylthioalkoxyacetyl, methylsulfonylhydroxyethyl, or methylsulfonylhydroxyethyl.

2. A compound of claim 1 wherein R is methylsulfonylacetyl.

3. A compound of claim 1 wherein R is methylsulfinylacetyl.

4. A compound of claim 1 wherein $X_{(n)}$ represents a monohalogenated substituent.

5. A compound of claim 1 wherein $X_{(n)}$ represents dihalogenated substituents.

6. A compound of claim 1 wherein $X_{(n)}$ represents trihalogenated substituents.

7. A compound of claim 1 wherein $X_{(n)}$ represents dihalogenated substituents and $Y_{(n)}$ represents a monohalogenated substituent.

8. A compound of claim 1 wherein $X_{(n)}$ represents 6-bromo-5-chloro, $Y_{(n)}$ represents zero and R represents methylsulfinylacetyl, said compound being 6-bromo-5-chloro-2[(methylsulfinyl)acetyl]-3-phenylindole.

9. A compound of claim 1 wherein $X_{(n)}$ represents, 5,6-dichloro, $Y_{(n)}$ represents 3,4-dichloro, R represents methylsulfinylacetyl, said compound being 5,6- dichloro-2-[(methylsulfinyl)acetyl]-3-(3,4-dichlorophenyl)indole.

10. A compound of claim 1 wherein $X_{(n)}$ represents 6-bromo-5-chloro, R represents methylsulfonylacetyl, said compound being 6-bromo-5-chloro-[(methylsulfonyl)acetyl]-3-phenylindole.

11. A compound of claim 1 wherein $X_{(n)}$ represents 5-chloro, Y represents 2-fluoro and R represents methylsulfinyl, said compound being 5-chloro-2-[(methylsulfinyl)acetyl]-3-(2-fluorophenyl)indole.

12. A compound of claim 1 wherein $X_{(n)}$ represents 6-bromo-5-chloro, $Y_{(n)}$ represents 2-fluoro and R represents methylsulfinyl, said compound being 6-bromo-5-chloro-3-(2-fluorophenyl)-2-[(methylsulfinyl)acetyl]indole.

13. A compound of claim 1 wherein $X_{(n)}$ represents zero, $Y_{(n)}$ represents 2-fluoro and R represents methylsulfinylacetyl, said compound being 5,6-dichloro-2-[(methylsulfinyl)acetyl]-3-phenylindole.

14. A compound of claim 1 wherein $X_{(n)}$ represents 4,5,6-trichoro and R represents methylsulfinylacetyl, said compound being 4,5,6-trichloro-2-[(methylsulfinyl)acetyl]-3-phenylindole.

15. A compound of claim 1 wherein $X_{(n)}$ represents 5-chloro, Y represents, 2,6-difluoro and R represents methylsulfinylacetyl, said compound being 5-chloro-2-[(methylsulfinyl)acetyl]-3-(2,6-difluorophenyl)indole.

16. A compound of claim 1 wherein $X_{(n)}$ represents 5-chloro, $Y_{(n)}$ represents 2,4-dichloro and R represents methylsulfinylacetyl, said compound being 5-chloro-2-[(methylsulfinyl)acetyl]-3-(2,4-dichlorophenyl)indole.

17. A method for treating rheumatoid arthritis which comprises administering to a mammal suffering from rheumatoid arthritis a therapeutically effective quantity of a compound having the formula

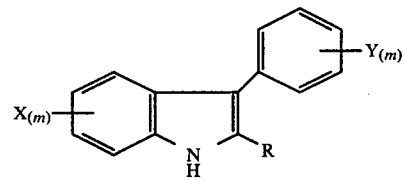

wherein each of X and Y are halogen, (n) is an integer of zero to three, and R is methylsulfinylacetyl, methylsulfonylacetyl, methylthiohydroxyacetyl, methylthioalkoxyacetyl, methylsulfinylhydroxylethyl, or methylsulfonylhydroxyethyl together with a pharmaceutically acceptable carrier.

18. A method of eliciting an immunosuppressant response in a mammal suffering from a disease state responsive to an immunosuppressant which comprises administering a therapeutically effective amount of a compound of the formula

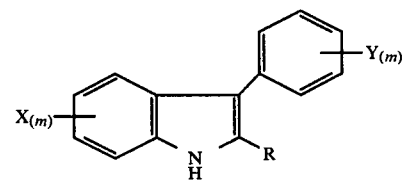

wherein each of X and Y are halogeno, (n) is an integer of zero to three, and R is methylsulfinylacetyl, methylsulfonylacetyl, methylthiohydroxyacetyl, methylthioalkoxyacetyl, methylsulfinylhydroxyethyl, or methylsulfonylhydroxyethyl together with a pharmaceutically acceptable carrier.

19. A pharmaceutical composition useful in treating rheumatoid arthritis or eliciting an ummuno suppressant response comprising an effective amount of a compound according to any one of claims 1 to 16 and a pharmaceutically acceptable carrier.

* * * * *